(12) United States Patent
Corbeil et al.

(10) Patent No.: US 11,154,262 B1
(45) Date of Patent: Oct. 26, 2021

(54) METHOD AND APPARATUS FOR MOUNTING AND ALIGNING DETECTORS OF A MEDICAL IMAGING APPARATUS

(71) Applicant: Siemens Medical Solutions USA, Inc., Malvern, PA (US)

(72) Inventors: James L. Corbeil, Knoxville, TN (US); Nicholas Gullette, Knoxville, TN (US); Jeffrey Bostrom, Clinton, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 28 days.

(21) Appl. No.: 16/946,514

(22) Filed: Jun. 25, 2020

(51) Int. Cl.
  *A61B 6/00* (2006.01)
  *A61B 6/03* (2006.01)

(52) U.S. Cl.
  CPC ............ *A61B 6/4435* (2013.01); *A61B 6/032* (2013.01); *A61B 6/037* (2013.01); *A61B 6/4417* (2013.01)

(58) Field of Classification Search
  CPC ....... A61B 6/4435; A61B 6/032; A61B 6/037; A61B 6/4417
  See application file for complete search history.

(56) References Cited

U.S. PATENT DOCUMENTS

| | | | |
|---|---|---|---|
| 8,581,196 B2 * | 11/2013 | Yamaya | A61N 5/1048 250/363.03 |
| 8,590,331 B2 | 11/2013 | Corbeil et al. | |
| 2015/0073272 A1 * | 3/2015 | Corbeil | A61B 6/4417 600/427 |
| 2017/0112454 A1 * | 4/2017 | Yun | A61B 6/0407 |

* cited by examiner

*Primary Examiner* — Michael C Bryant

(57) ABSTRACT

Detector heads in a gantry of a medical imaging apparatus are pivotally-coupled to mounting rails oriented axially about the gantry's axial centerline. Radial alignment blocks facilitate alignment and fixation of detector faces circumferentially transverse and normal to a radius projecting from the gantry's axial centerline. A column of detector heads on a common rail are separated by axial stop blocks, for precise axial separation. Abutting detector heads on a common mounting rail are slaved to another previously transverse-aligned detector through a common, shared radial alignment block. Plural, stacked gantry backplanes are fabricated simultaneously, assuring common circumferential and radial co-registration of plural mounting rails relative to the axial centerline of the gantry. Adjustable orientation of the detector heads compensates for tolerance stack up during final assembly of the gantry, so that the detector heads are mutually aligned in a uniform grid of axial columns and circumferential rows.

20 Claims, 7 Drawing Sheets

METHOD AND APPARATUS FOR MOUNTING AND ALIGNING DETECTORS OF A MEDICAL IMAGING APPARATUS

TECHNICAL FIELD

This disclosure relates to medical imaging apparatus. More particularly, this disclosure relates to methods and apparatuses for mounting and aligning photonic detectors in gantries of medical imaging apparatuses.

BACKGROUND

Diagnostic medical imaging apparatuses include, by way of non-limiting example, computed tomography (CT) and positron emission tomography (PET) modalities, as well combination PET/CT modalities. Many of these imaging apparatuses or systems include a gantry structure with a toroidal- or cylindrically-shaped central passage, through which is inserted a patient table. The gantry includes a three-dimensional, generally cylindrically-oriented array of electromagnetic radiation detector heads, each of which emits electrons in response to incident photons of electromagnetic radiation on a corresponding detector surface of the device. The output electrons of each detector are processed by detector electronics to generate detector output signals. The plural detector output signals are subsequently processed by the imaging apparatus to generate patient images. Image quality improves when the detector surface of each detector head is spatially oriented in a virtual circle that is transversely normal to and at a common radial length from an axial centerline of the gantry. When so oriented, all of the detector surfaces are in uniform, three-dimensional co-alignment, axially, radially, and circumferentially, with respect to the gantry's axial centerline, enhancing potential image quality.

In order to achieve uniform, three-dimensional co-alignment among the respective detector surfaces, the detector heads and their mounting structure within a gantry are constructed with high manufacturing tolerances. In exemplary PET modalities, alignment of PET detector heads is established by component dimensions generally inherent to the design, with no ability to compensate for or offset manufacturing tolerances once the heads are mounted on the gantry. The spatial positional accuracy of the fundamental imaging unit, a pixel, is therefore defined by the sum of tolerances of the components of gantry frame, of the PET detector head, of the mechanical interface between the frame and detector head and of the method by which the PET system is aligned other components of the medical imaging apparatus, such as the CT components in a combination PET/CT modality apparatus. For an imaging system with only one or two circumferential rows of detector heads, this poses a small risk to the image quality, as most machining and assembly tolerances can be held, within the margin of error required by subsequent image processing, at reasonable manufacturing cost. However, recent movement in the field of PET imaging, with field of view (FOV) expansion of the patient imaging approaching one to two meters, has made it necessary to revisit the nature of both the design and the machining such systems, including in exemplary PET/CT systems. Often these axially expanded systems require a plurality of gantry frames and gantry backplanes, further complicating the detector head spatial alignment issue. It becomes economically averse to machine existing designs of each gantry component and detector mount to even tighter than presently established tolerances, in order to enable the larger 1-2 m FOV systems to maintain positional accuracy achieved in known, smaller FOV systems.

SUMMARY

Exemplary embodiments described herein correct for tolerance stack up during final assembly of a gantry of a medical imaging apparatus, such as a PET or PET/CT imaging system. Embodiments described herein facilitate a degree of detector head three-dimensional, spatial positional accuracy, at lower cost compared to more precisely machined, higher manufacturing tolerance systems. One or more detector heads is pivotally-coupled to respective mounting rails, with a plurality of the mounting rails circumferentially spaced about the gantry/gantry frame, which facilitates aligning and orienting respective detector faces transverse to the axial centerline of the gantry within a range of pivotal motion, i.e., normal to a radius between the centerline of the gantry frame and the detector face. A locking mount selectively locks the detector head in any desired pivotal alignment position. In some embodiments, radial alignment blocks facilitate transverse alignment of the detector faces. In some of those embodiments, a reference marking or registry surface of the radial alignment block is oriented co-axial with the radius between the gantry centerline and the detector face. In multi-detector rail applications, a column of detector heads, mounted on a common rail, are separated by axial stop blocks, which assures precise axial separation of their detector surfaces. In some embodiments, abutting detector heads on a common mounting rail are slaved to another previously transverse-aligned detector through a common, shared radial alignment block. In this way, the slaved detector heads are aligned transversely with respect to the axial centerline of the gantry, in common with the master, previously aligned detector head. In some embodiments, plural mounting rails are circumferentially aligned about gantry backplanes of the gantry. In some embodiments, fabrication of plural, stacked gantry backplanes having commonly co-registered mounting-rail affixation surfaces, assures common circumferential co-registration of plural mounting rails commonly radially spaced from the axial centerline of the gantry, at common clocked positions about the gantry circumference after final assembly.

Exemplary embodiments feature a detector mounting and alignment system for a medical imaging apparatus, comprising a gantry. The gantry includes a gantry frame defining an axial centerline, an outer periphery, and a cylindrical-shaped inner circumference defining a patient imaging passage. In some embodiments, the gantry frame comprises a cylindrical tube structure. In other embodiments, the gantry frame comprises one or more gantry backplanes oriented between the outer periphery and the inner circumference of the gantry frame. In such embodiments incorporating one or more gantry backplanes, a mounting rail is coupled to the gantry backplane between the outer periphery and the inner circumference of the gantry frame. The mounting rail has a rail central axis oriented parallel to the axial centerline of the gantry frame. A detector head is pivotally coupled to the mounting rail, having a range of pivotal motion about a detector pivot axis that is parallel to the rail central axis. The detector head has a photon detector surface facing the axial centerline of the gantry frame. A locking mount of the detector head couples the detector head and the gantry frame, for selectively locking the detector head at any desired fixed position within its range of pivotal motion. In some embodiments, there are plural mounting rails circumferentially spaced about the gantry frame. In some embodiments, a plurality of detector heads are coupled to one or more of the mounting rails. In other embodiments, plural gantry frames are coupled in tandem, with coaxial gantry frame centerlines and pluralities of co-registered, mounting rails and detector heads, having respective rail central axes that are oriented parallel to the gantry frame coaxial centerlines.

Other exemplary embodiments feature methods for mounting and aligning a detector in a gantry of a medical imaging apparatus. In one embodiment, the gantry frame defines a patient imaging passage. A mounting rail, having a rail central axis, is coupled to the gantry frame, oriented between an outer periphery and a cylindrical-shaped inner circumference of a gantry frame, so that a central axis of the rail is oriented parallel to an axial centerline defined by the gantry frame. A first axial stop-block is coupled to the mounting rail intermediate first and second ends of the rail. A first detector head is pivotally coupled to a first detector bearing so that the first detector head has a range of pivotal motion about a first detector pivot axis. The first detector head has a first photon detector surface, and a first radial alignment block having a first radial alignment axis normal to the first photon detector surface. The first radial alignment block is selectively aligned with respect to a radius normal to the gantry frame's axial centerline, so that the first photon detector surface is transversely normal that axial centerline. The first detector bearing is inserted on the first end of the mounting rail, and slid along the rail until it abuts the first axial stop-block, with the first detector head oriented on the mounting rail with the first detector pivoting axis parallel to the rail central axis and the first photon detector surface facing the axial centerline of the gantry frame. The first detector head is pivoted, while aligning the first photon detector surface with the first radial alignment block, so that the first photon detector surface is oriented transversely normal to the axial centerline of the gantry frame. After the first detector head is so aligned, it is locked in fixed position, with a locking mount coupled thereto of the gantry frame. In some embodiments, plural mounting rails are coupled to the gantry, circumferentially spaced about the gantry frame. In some embodiments, a plurality of detector heads are coupled to one or more of the mounting rails. In other embodiments, plural gantry frames are coupled in tandem, with coaxial gantry frame centerlines and pluralities of co-registered, mounting rails and detector heads, having respective rail central axes that are oriented parallel to the gantry frame coaxial centerlines.

The respective features of the exemplary embodiments that are described herein may be applied jointly or severally in any combination or sub-combination.

BRIEF DESCRIPTION OF DRAWINGS

The exemplary embodiments are further described in the following detailed description in conjunction with the accompanying drawings, in which.

To facilitate understanding, identical reference numerals have been used, where possible, to designate identical elements that are common to the figures. The figures are not drawn to scale.

DESCRIPTION OF EMBODIMENTS

Exemplary embodiments are utilized in expanded FOV systems having multiple, tandem gantry frames coaxially aligned with each other. In some embodiments, manufacturing tolerance error of the gantry frame components is reduced through the use of one or more cylindrical-shaped gantry tubes. In other embodiments that incorporate gantry backplanes, manufacturing tolerance error of the gantry frame components is reduced by stacking two or more gantry backplanes, then machining or otherwise fabricating them as a co-joined structure. The co-machined parts are affixed to a common support base such that they are co-registered circumferentially and radially relative to the axial centerline of the gantry frame. By machining and fixing critical alignment datums in the assembled gantry frame, whether formed of one or more cylindrical tubes and/or backplanes, such as rail mounting affixation surfaces, in such a manner, tolerance stacking errors that would otherwise be inherit to individually machined parts are avoided. Mounting and axially spacing a column of detector heads on a common rail co-axially aligns detector surfaces in each detector head, for their precise radially alignment relative to the gantry frame's axial centerline. Precisely orienting plural rails circumferentially about the gantry backplanes, so that the rail axis of each is parallel to each other and the gantry frame's axial centerline, enables precise column and row alignment of each column and row of detector surfaces of each detector head in a uniform grid pattern. The uniform grid pattern in this extended FOV imaging system enables similar imaging quality as is realized with existing smaller FOV imaging systems. An embodiment of an extended FOV medical imaging system is shown in FIGS. 1-3.

Figure 1:
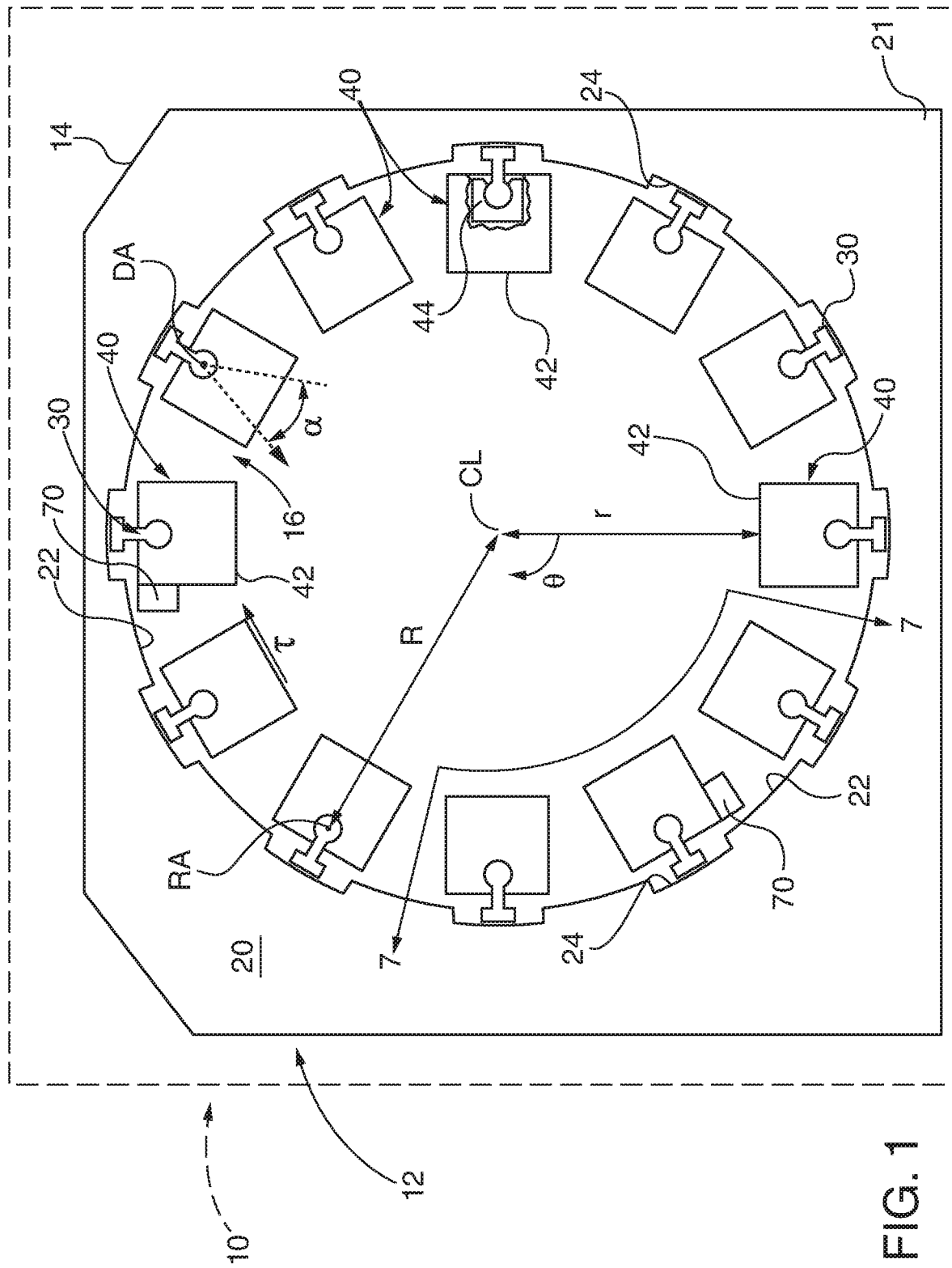
FIG. 1 is an axial elevational view of a medical imaging apparatus, its gantry, including gantry frame, and a circumferential array of detector heads.
Figure 2:
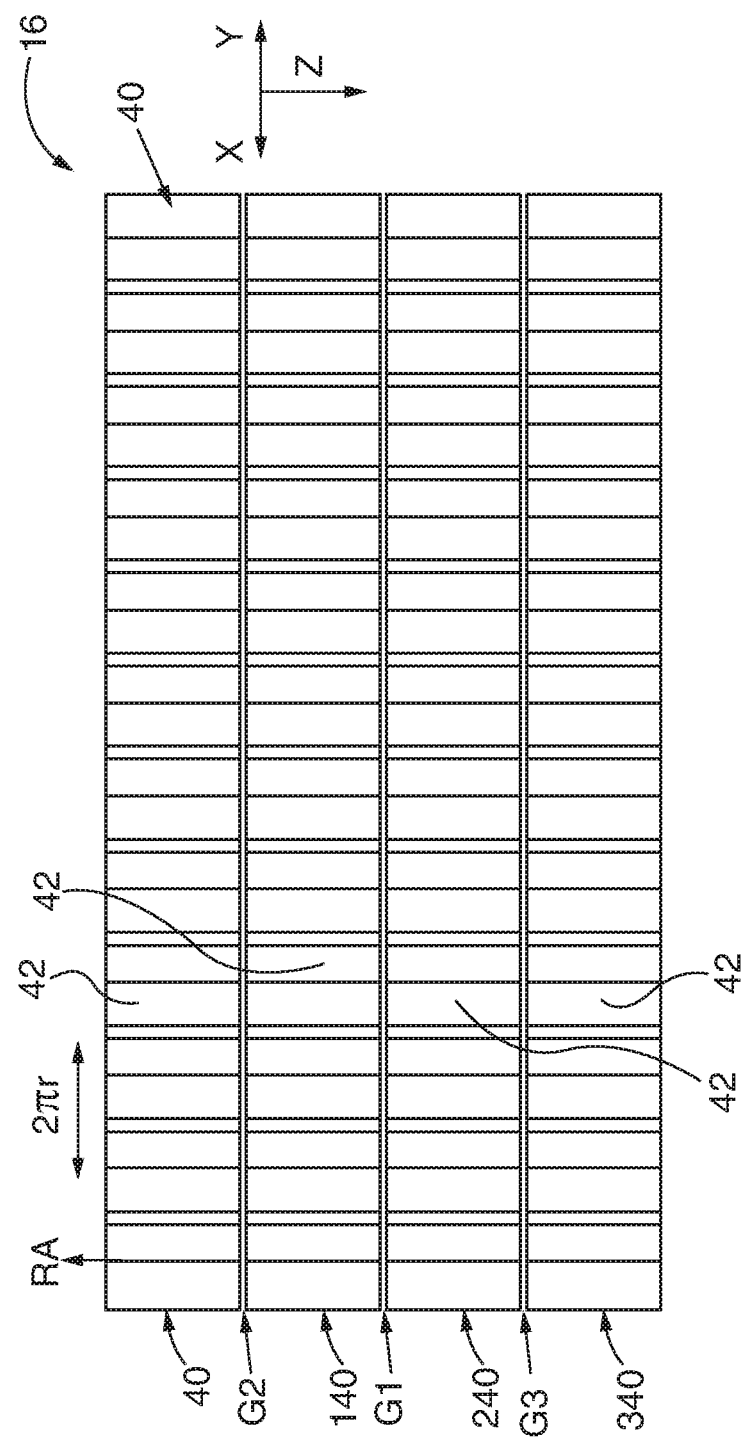
FIG. 2 is a flat projection of the two-dimensional grid of the circumferential array of detector heads of the medical imaging apparatus of FIG. 1.
Figure 3:
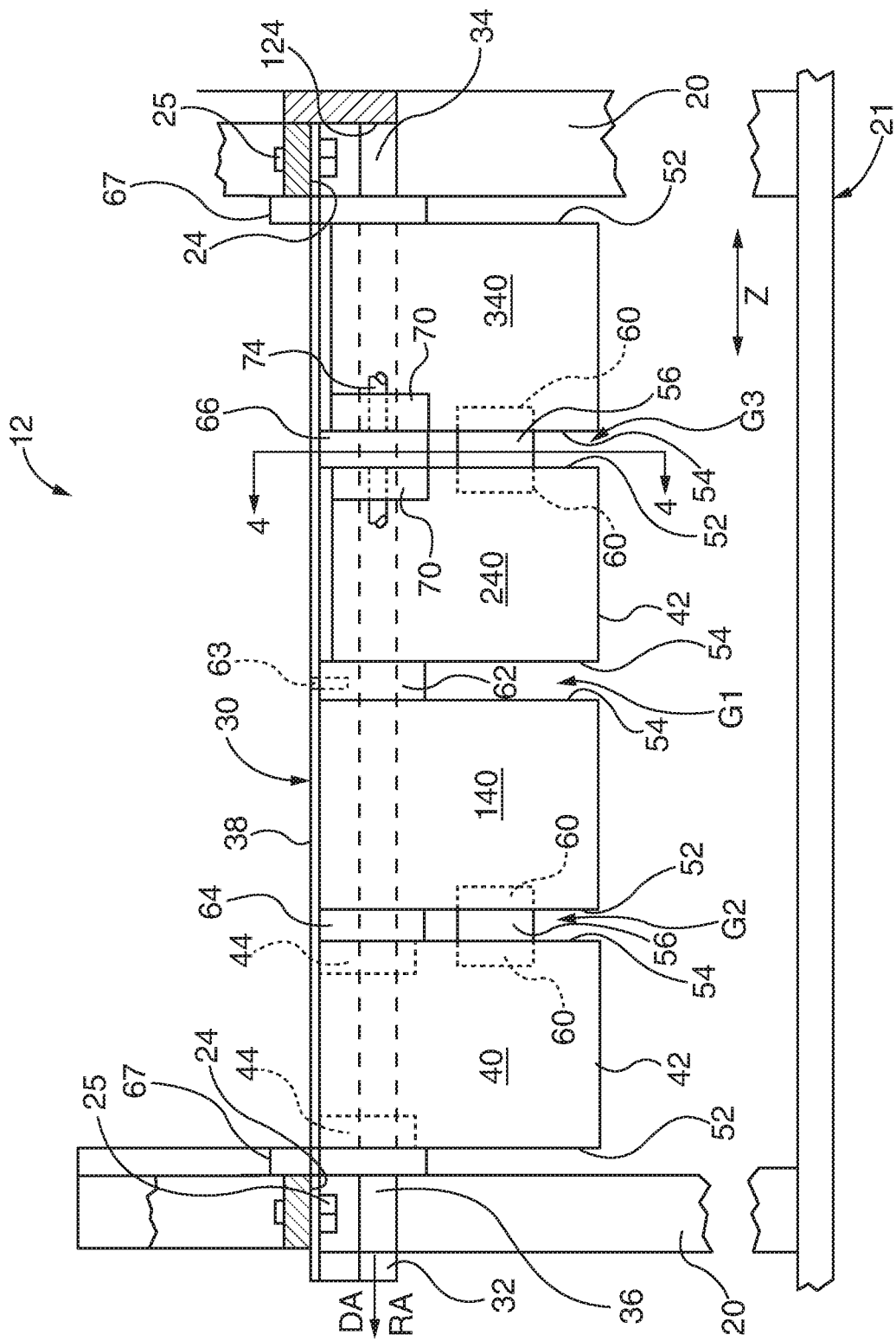
FIG. 3 is a side elevational view of a detector mounting rail and a column of four detectors, of the medical imaging apparatus of FIG. 1.

In FIGS. 1-3, an extended FOV, PET imaging system 10 includes a gantry 12, which incorporates a gantry frame comprising backplanes 20 coupled in axially parallel orientation to a base plate 21. The gantry 12, including its gantry frame, defines an axial centerline CL, an outer periphery, 14 and a cylindrical-shaped inner circumference 16 defining a patient imaging passage. The backplanes 20 are spanned by multiple circumferentially spaced mounting rails 30, each having a rail central axis RA oriented parallel to the axial centerline CL of the gantry 12. The mounting rails 30 are coupled to affixation surfaces 24, 124 formed in the inner, cylindrical circumference 22 of the pair of backplanes 20. In some embodiments, identically oriented affixation surfaces 24, 124 are formed in each pair of opposed backplanes 20, so that the mounting rails 30 are commonly clocked circumferentially about the gantry 12, radially with respect to the gantry's axial centerline CL, and axially with respect to an axial plane normal to that axial centerline. Identically formed backplanes 20 facilitate parallel alignment of the rail central axis RA each mounting rail 30 with respect to the axial centerline CL. Other gantry frame embodiments (not shown) incorporate a cylindrical tube without use of backplanes 20, in which the mounting rails 30 are directly or indirectly coupled about the inner circumference of the cylindrical tube.

A plurality of detector heads 40, 140, 240, 340 are pivotally coupled to each mounting rail 30, with each detector head having a range of pivotal motion a about a detector pivot axis DA that is parallel to the rail central axis RA. In some embodiments, the range of motion a is identical for all of the detector heads 40, 140, 240, 340, while in other embodiments various detectors have different ranges of pivotal motion. While four detector heads share a common mounting rail 30 in this exemplary embodiment, other embodiments mount as few as one or a plurality of two or more detector heads to the mounting rail. Other embodiments mount more than four detector heads to a common mounting rail. Each of the detector heads 40, 140, 240, 340 has a photon detector surface 42 facing the axial centerline CL of the gantry frame 12. At least one locking mount 70 is coupled to the gantry 12 proximate each mounting rail 30, for selectively locking one or more of the detector heads 40, 140, 240, 340 at any desired fixed position within its range of pivotal motion α. The locking mount 70 is also directly coupled to a single detector head, or indirectly coupled to one or more other detector heads 40, 140, 240, 340 on their common mounting rail 30. The locking mounts 70 align the photon detector surface 42 of each detector head at a tangent τ to a virtual circle defined by the radius r that projects from the axial centerline CL of the gantry/gantry frame 12 and each detector surface. Thus, each detector surface 42 is aligned in a plane that is transverse or normal to the axial centerline CL. In the embodiment of FIGS. 1-3, the radius r between the axial centerline CL and the central axis RA of each mounting rail 30 is coaxial with the radius r. In other embodiments, the radius between central axis of the mounting rail and the axial centerline of the gantry is offset from the radius of the detector surface to the gantry's axial centerline.

Referring to FIG. 2, the inner circumference 16 of the gantry 12 is unwrapped in a planar projection. In the axial or Z direction, a column of detectors 40, 140, 240 and 340 are commonly coupled to mounting rail 30. Referring to FIGS. 1 and 2, by virtue of their common rail mount the detector surface 42 of each detector head is axially aligned along its rail central axis RA along a single degree of freedom, so there is no significant lateral staggering (i.e., left-right in FIG. 2) of the respective detector surfaces. While each individual detector surface 42 is aligned transversely normal τ to the axial centerline CL of the gantry/gantry frame 12 relative to the radius r, the amount of lateral staggering between columns of detectors that is attributable to such pivotal alignment variance a deviates less than one pixel width of resolution between laterally adjoining detector surfaces. The plurality of detector heads in each column are also oriented in sequential rows 40, 140, 240 and 340 in the X-Y cartesian or Θr polar axes. The detector surfaces 42 in each row of detector heads is identically axially spaced within precise tolerance in the gaps G1, G2 and G3, by precise axial spacing of the respective detector heads 40, 140, 240 and 340 on each mounting rail 30 to within one pixel width or less of axial resolution.

Figure 4:
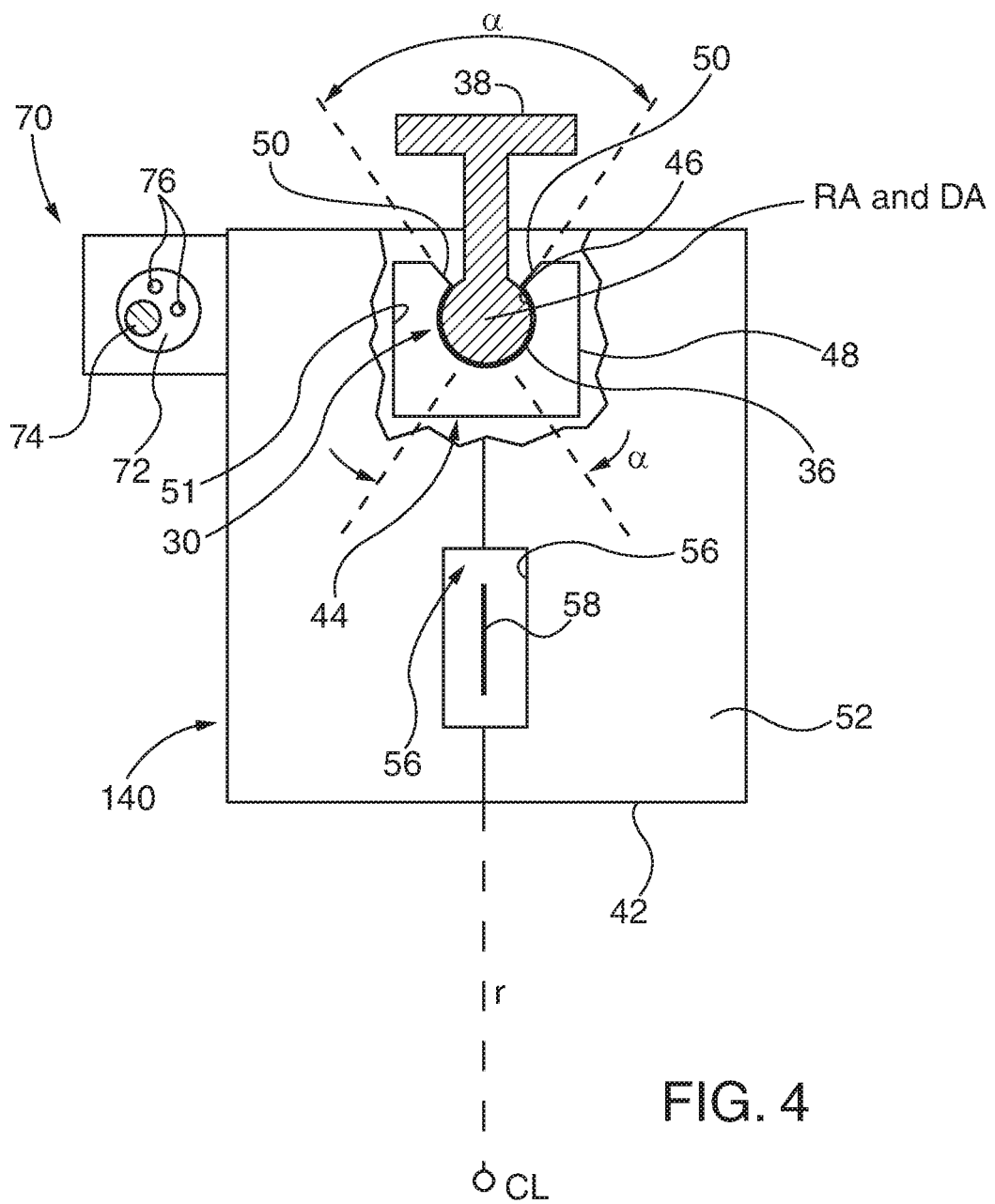
FIG. 4 is a cross-sectional view of the detector mounting rail and a detector of FIG. 3, along 4-4 thereof.
Figure 5:
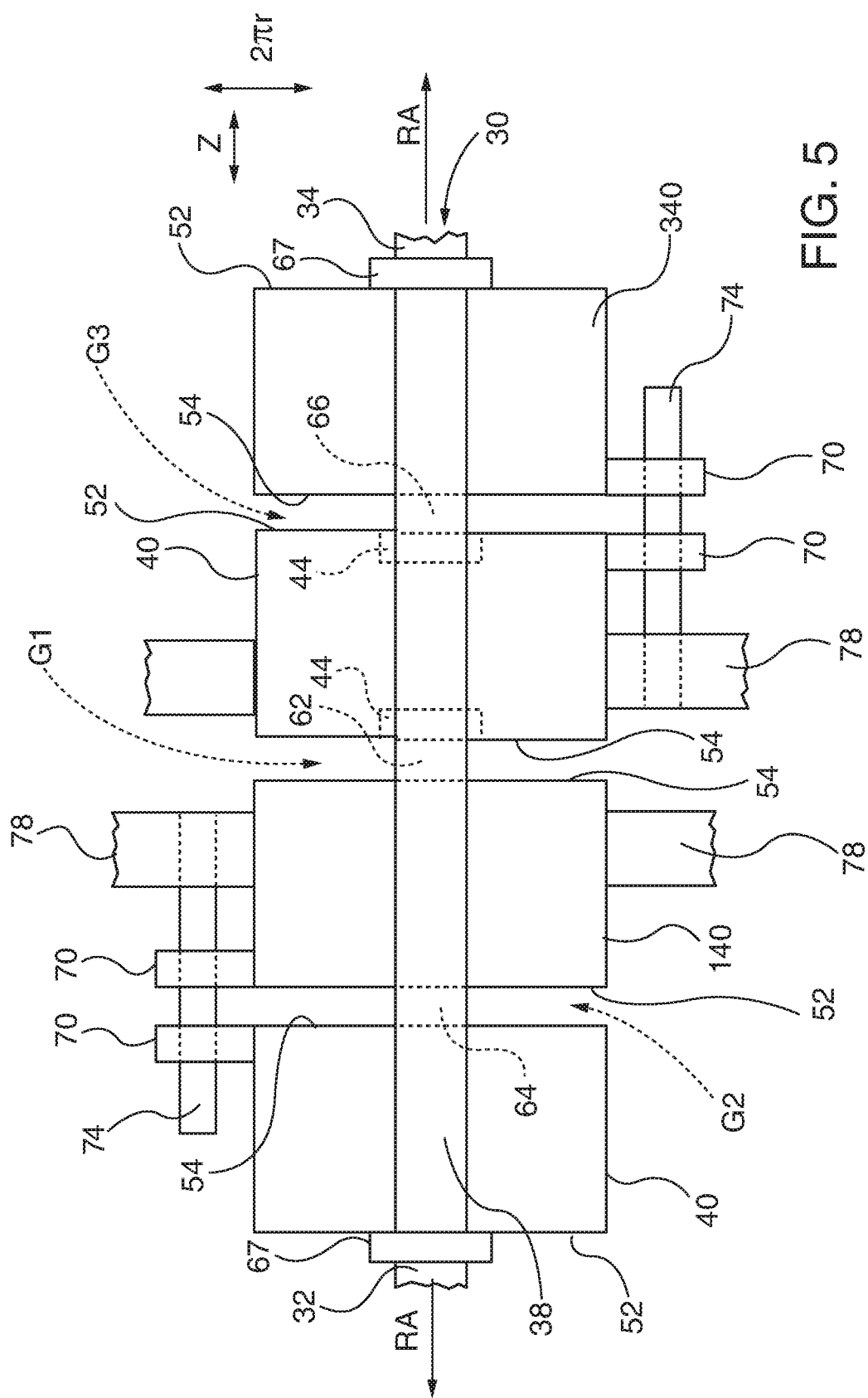
FIG. 5 is a top plan view of the detector mounting rail and column of four detectors of FIG. 3.

An exemplary mounting and alignment system apparatus for achieving precise lateral and axial alignment of plural detector surfaces 42 within one pixel or less of resolution is shown in FIGS. 3-5. For brevity, unless otherwise specified to the contrary, future reference to a "detector heads" means one or more or all of the detector heads 40, 140, 240, 340.

The four detector heads are commonly mounted on a single mounting rail 30. The first 32 and second 34 ends of the mounting rail 30 are coupled by machine screws 25 to corresponding affixation surfaces 24, 124 in the pair of opposed backplanes 20, so that its central axis RA is parallel to the axial centerline CL of the gantry 12, including the backplanes. In other embodiments, different profiles of rail affixation surfaces and fastening components are used to affix one or more of the mounting rails to the backplane, and in yet other embodiments, one or both ends of the mounting rails overhang one or more of the backplanes, in cantilever-like fashion.

The profile of the mounting rail 30 comprises a cylindrical head surface 36 and a flange 38 that abuts the corresponding affixation surfaces 24 of each respective backplane 20. The profile of the mounting rail 30 structure of this embodiment is a commercially available linear rail commonly used in linear motion control apparatus, though in other embodiments other rail profiles and structures are utilized.

Each of the detector heads 40, 140, 240, 340 is pivotally mounted to the mounting rail 30 by a pair of detector bearings 44. Each detector bearing 44 has an inner, sector-shaped cross-sectional profile, with an inner circumferential surface 46 of the bearing circumscribing a portion of the cylindrical-profile surface portion 36 of the mounting rail 30. An outer peripheral surface 48 of the bearing 44 is coupled to the detector head. Mutually opposed, spaced radial stop surfaces 50 of the bearing abut the mounting rail at respective extreme terminus positions along the pivotal range of motion a of the detector head. The outer surface 48 of each bearing 44 is retained within respective bearing recesses 51 formed in respective first 52 and second 54 axial ends of the detector head. The detector bearing 44 of this embodiment is a commercially available linear bearing, commonly used in linear motion control apparatus, which slidably mounted on the corresponding mounting rail 30; though in other embodiments other bearings are utilized. For example, in alternative embodiments, one or more pivot bearings are clamped or otherwise affixed to the mounting rail at defined axial locations. Yet in other embodiments, one or more bearings are integrally formed in a detector head, such as in end plates of the detector head (not shown), obviating the need for a separate bearing structure to be coupled to the detector head. While in the embodiments of FIGS. 3-5, the bearing pivot axis DA is coaxial with the mounting rail central axis RA, in other embodiments those respective axes are offset from each other. In other embodiments, various detector heads are pivotally mounted to its corresponding mounting rail by one detector bearing or more than two detector bearings.

A radial alignment block 56 incorporates a radial-alignment surface feature or reference datum 58, and is received in a recess 60 formed at least one of the respective first 52 and second 54 axial ends of a detector head. When a radial alignment block 56 is received within a detector head recess 60, its radial-alignment surface feature 58 defines a radial alignment axis normal to the photon detector surface 42 of the corresponding detector head. By aligning the surface feature 58 coaxial with the radius r within the detector head's range of pivotal motion a, the corresponding photon detector surface 42 is aligned transversely normal τ to the axial centerline CL of the gantry/gantry frame 12.

As previously described, the PET imaging apparatus 10 axially positions the detector surface 42 in each axial column of detector heads at precise axial gaps G1, G2, and G3. Axial stops positioned at defined axial locations along the length of each mounting rail 30 facilitate replication of each of the aforementioned axial gaps (also referred to as axial tolerance reset) on each respective mounting rail. As shown in detail in FIGS. 2, 3 and 5, a first axial stop-block 62 is slidably inserted about the cylindrical surface 36 and then rigidly coupled to the flange 38 of the mounting rail 30 with pins 63, approximately midway between the first 32 and second 34 ends of the mounting rail. In other embodiments, the first axial stop-block 62 is not rigidly coupled to the flange 38 or any other portion of the mounting rail 30, allowing detectors in the associated column on the mounting rail to be shifted axially in the Z direction to any desired position. Detector heads 140 and 240 abut opposite axial surfaces of the first stop block 64, to establish the axial gap G1 in the grid of detector surfaces 42 of FIG. 2. In other embodiments, the first axial stop block 64 is affixed to the mounting rail 30 by clamps, screws, welds, adhesive or other known affixation methods.

A second axial stop block 64 is slidably inserted on the cylindrical surface 36 at the first end 32 of the mounting rail 30, until it abuts the first axial end 52 of detector head 140. The second axial end 54 of detector head 40 abuts the second axial stop block 64, establishing the axial gap G2 between the adjoining detector surfaces 42 of the detector heads 40 and 140.

Similarly, a third axial stop block 66 is slidably inserted on the cylindrical surface 36 at the second end 34 of the mounting rail 30, until it abuts the first axial end 52 of detector head 240. The second axial end 54 of detector head 340 abuts the third axial stop block 66, establishing the axial gap G3 between the adjoining detector surfaces 42 of the detector heads 240 and 340.

In some embodiments, axial ends of one or more of the axial stop blocks 62, 64 and/or 66 are received with a recess formed in the first 52 and/or second 54 end of the corresponding detector head, establishing precise axial datums between the adjacent heads. Once the detector heads 40, 140, 240, 340 are aligned in abutting contact with their respective axial stop blocks 62, 64, 66 they are axially locked in place in the Z direction by end caps 67 coupled to the respective first 32 and second 34 axial ends of the mounting rail 30. The end caps 67 prevent relative axial shifting of adjacent detectors surfaces 42 within a column of detectors. In some embodiments, the end caps 67 are pinned or clamped to the mounting rail 30. In some embodiments, the respective end caps 67 are spring biased or incorporate a threaded clevis to bias the detector heads 40, 140, 240, 340 in abutting contact in the Z direction. In some embodiments, the combination of a slidable, non-rigidly coupled, first axial stop-block 62 and an end cap 67 selectively shift relative axial location of that "floating" stop-block along the rail. In other embodiments, various "floating" first axial stop-blocks 62 are oriented at varying (e.g., staggered axial locations on different mounting rails 30. The respective axial ends of the axial stop blocks 62, 64, 66 define mutually parallel, axial-stop planes between the respective rows detector heads 40, 140, 240, 340, with the axial length of each stop block defining its associated axial gap G1, G2, G3 of the detector grid shown in FIG. 2. In lieu of the use of one or more of the axial stop blocks 62, 64, 66 or the end caps 67, individual detector heads in other embodiments are rigidly affixed in specific axial positions on a mounting rail by other means, such as clamps, screws, welds, pins, mating detents/pawls, and the like.

Referring to FIG. 2, as the axial locking process is completed for each mounting rail 30, axial spacing of all pixels of each detector surface 42 that is commonly mounted on the rail are aligned, no matter how many detector heads (i.e., 1-4 or more detector heads) are mounted on that rail, within the grid column. Thus, after assembly of the gantry 12, relative pixel alignment in the Z direction is established, leaving the need to establish uniform pixel alignment, in the X-Y or re dimensions of the detector surfaces 42 within the detector grid.

Referring to FIG. 4, alignment of the detector surface 42 normal to the axial centerline CL of the gantry/gantry frame 12, is accomplished by pivoting the associated detector head 140 along the pivot axis DA within its range of pivotal motion a, until the radial alignment axis 58 of the radial alignment block 56 is coaxial with the radius r between the detector surface and the axial centerline. Once the desired radial alignment of the detector surface 42 is achieved the detector head 140 is locked with an associated locking mount 70. The same alignment procedure is performed with other detector heads that have associated radial alignment blocks 56.

Referring to the embodiment of FIGS. 3-5, a locking mount 70 is coupled to the first axial end 52 of detector 140 and another locking mount is coupled to the first axial end 52 of detector 240. Each locking mount 70 comprises an eccentric 72. The offset hole or bearing surface in the eccentric receives a support rod 74. The support rod 74 is coupled to a gantry support 78 and oriented parallel to the mounting rail axis RA. As the eccentric 72 is adjusted by rotation about the support rod 74, it levers the corresponding detector head 140, 240 about its pivoting axis DA, along the pivoting range of motion a. Once either or both of the detector heads 140, 240, is pivotally aligned so that the radial-alignment surface feature 58 of its respective radial alignment block 56 is coaxial with the radius r between the detector surface and the axial centerline its associated detector head 240, the associated locking screws 76 are tightened. The locking mount 70 also functions as a tangential alignment and fixation "spacer" for each associated column of detector heads 40, 140, 240, 340 about the circumference of the backing planes 20, so that each column does not pivot freely about the detector pivot axes DA after locking its respective locking mount. This maintains the tangential or lateral gap between adjoining detectors in a row of detectors. The pivoting detector head and locking mount features described with respect to the FIGS. 3-5 are suitable for positioning one or more detector heads within a medical imaging apparatus.

Figure 6:
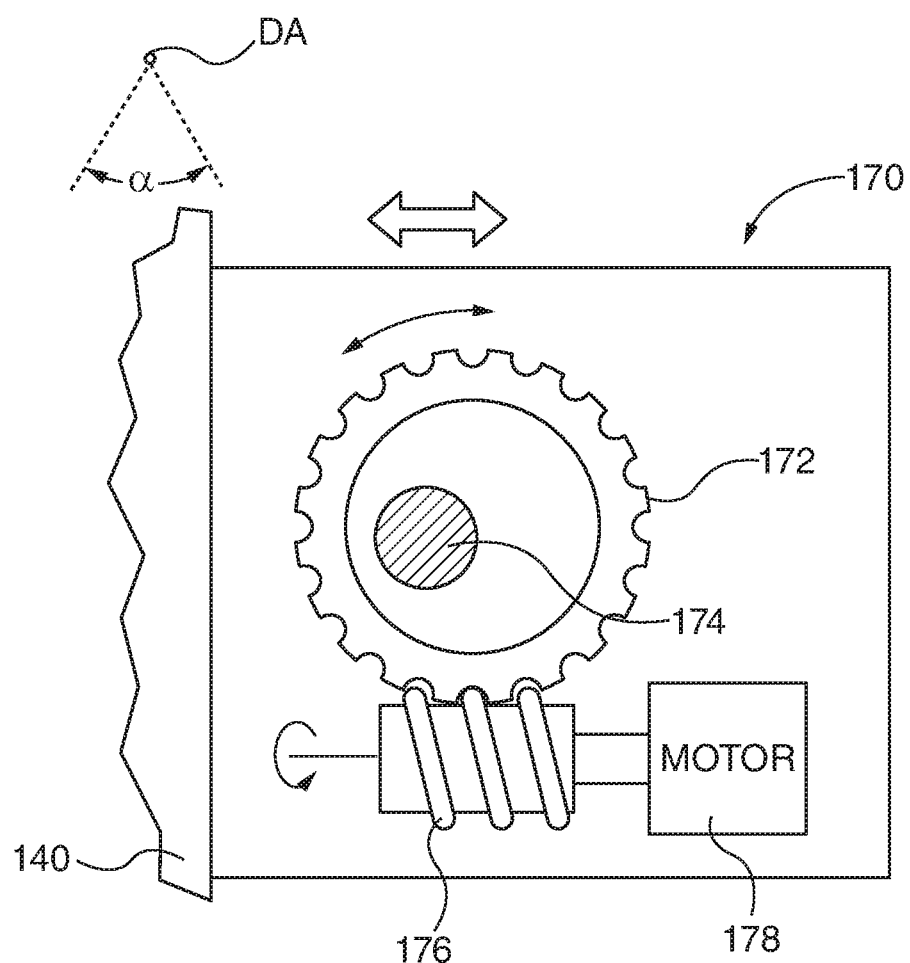
FIG. 6 is an elevational view of an embodiment of a locking mount of a detector head.

In the locking mount 174 embodiment of FIG. 6 an eccentrically mounted, toothed gear 172 rotates about a support shaft 174 of detector head 140, driven by mating worm gear 176. While the worm gear 176 is driven by a mounted electric motor 178, in alternative embodiments, it is driven directly or remotely (e.g., by drive shaft or drive cable) by a hand tool, hand crank or motor. In other embodiments, the locking mount comprises a ratcheting mechanism to rotate the toothed gear 172. In other embodiments, the locking mount comprises a hydraulic or pneumatic cylinder, a linear or step motor, or a threaded rod and clevis linkage. In other embodiments, the locking mount for selectively locking any one or more detector heads at any desired fixed position within its range of pivotal motion comprises shims, wedges, jack screws and/or clamps that are interposed between the detector head and the gantry frame. In other embodiments, the locking mount comprises a second mounting rail, such that one or more detector heads are coupled to both mounting rails by bearings; pivot angle α is selectively varied by changing relative radial position r of the mounting rail pair.

In the embodiments of FIGS. 3-5, the now transversely aligned and locked detector heads 140 and 240 are master heads for respective associated slaved detector heads 40 and 340, which are thereafter coupled to the mounting rail 30. As the slaved detector heads 40 and 340 are slid onto the mounting rail 30, their associated radial alignment-block recesses 60 formed in their respective second detector ends 54 are aligned with and receive the corresponding radial alignment block 56 that projects from the respective first detector ends 52 of their corresponding master detector heads 140 and 240. Similarly, during installation of the slaved detector heads 40 and 340, their associated locking mounts 70 are aligned with and receive the support rod 74. The corresponding detector surfaces 42 of the slaved detector heads 40 and 340 are now also aligned transversely with respect to the axial centerline CL of the gantry/gantry frame 12. The locking mounts 70 associated with the slaved detector heads 40 and 340 are now tightened. Now the respective detector surfaces 42 of each of the detector heads 40, 140, 240, 340 in the axial column associated with the mounting rail 30 is now normal to, and spaced at equal radial distance r, relative to the axial centerline CL of the gantry/gantry frame 12. The transverse alignment process is repeated for all of the respective mounting rails 30 in the gantry/gantry frame 12 of FIGS. 1 and 2. Upon completion of the transverse alignment process for all mounting rails 30, all of the pixels in the grid of detector surfaces 42 of each respective, separate row of detectors (e.g., row 40, row 140, row 240, and/or 340) in the gantry grid are laterally aligned in the X-Y or rΘ coordinate directions.

Figure 7:
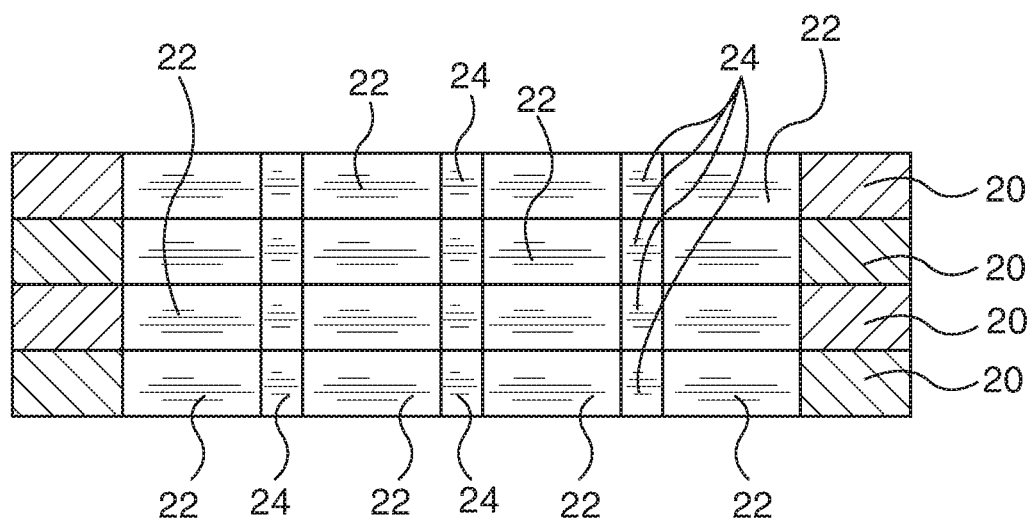
FIG. 7 is a partial cross-sectional view of four stacked gantry backplanes of FIG. 1 commonly fabricated in accordance with an embodiment of a manufacturing method described herein.

As previously discussed, it is desirable to utilize identical, paired backplanes 20 to construct the gantry/gantry frame 12 of the medical imaging apparatus of FIGS. 1-5. In this way the respective corresponding mounting rail affixation surfaces (e.g. 24, 124) on each pair of backplanes 20 are identically oriented radially and axially, assuring identical, parallel alignment of the central axis RA of each mounting rail 30 and the axial centerline CL of the backplanes 20/gantry/gantry frame 12. In FIG. 7, a vertical stack of four aligned backplanes 20 are commonly machined, so that each respective mounting rail affixation surface 24 of all four are oriented axially and circumferentially about their respective inner circumferences 22. The sector-shaped portion of each backplane corresponds to the cross-sectional reference 7-7 of FIG. 1. In some manufacturing embodiments, at least two or more than four stacked backplanes 20 are commonly machined. It is desirable to machine or otherwise fabricate as many stacked backplanes are needed to construct a medical imaging apparatus.

Figure 8:
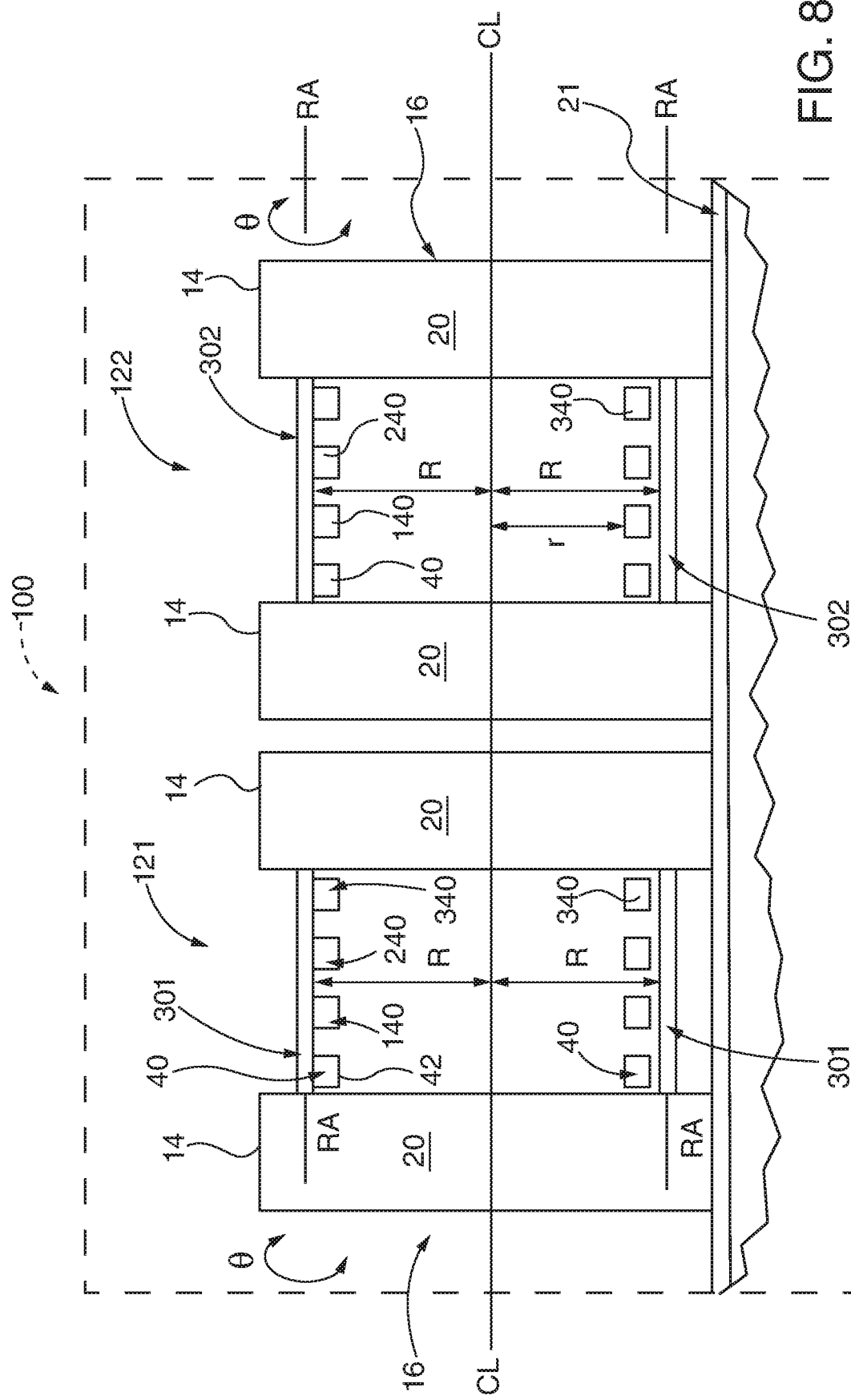
FIG. 8 is a side elevational, cutaway view of another embodiment of a medical imaging apparatus that incorporates two pairs of tandemly oriented gantry backplanes coaxially aligned having commonly co-registered mounting rails and columns of axially aligned detector heads.

The medical imaging apparatus 100 of FIG. 8 is a wide FOV, PET scanner, comprising two axially tandem gantry frames 121 and 122, sharing a common coaxial axial centerline CL. Each of respective pluralities of corresponding tandem-oriented pairs of circumferentially spaced mounting rails 301 and 302 of each gantry 121, 122 are coaxially registered on their commonly machined backplanes 20, so that they share a common, coaxial rail axis RA that is oriented parallel to and identically radially spaced R from the common coaxial axial-centerline CL of the gantry frames 121, 122. In this way all of the detector surfaces 42 of all of the detector heads 40, 140, 240, 340 on each rail 301, 302 are axially spaced relative to each other in a uniform grid pattern of axially aligned columns and circumferentially aligned in rows at equally spaced angles, and with all detector surfaces oriented transversely normal to the coaxial centerline CL of the gantry frames along a common radius r.

Although various embodiments that incorporate the invention have been shown and described in detail herein, others can readily devise many other varied embodiments that still incorporate the claimed invention. The invention is not limited in its application to the exemplary embodiment details of construction and the arrangement of components set forth in the description or illustrated in the drawings. The invention is capable of other embodiments and of being practiced or of being carried out in various ways. In addition, it is to be understood that the phraseology and terminology used herein is for the purpose of description and should not be regarded as limiting. The use of "including", "comprising", or "having", and variations thereof herein is meant to encompass the items listed thereafter and equivalents thereof as well as additional items. Unless specified or limited otherwise, the terms "mounted", "connected", "supported", and "coupled" and variations thereof are to be interpreted broadly they encompass direct and indirect mountings, connections, supports, and couplings. Further, "connected" and "coupled" are not restricted to physical, mechanical, or electrical connections or couplings.

What is claimed is:

1. A detector mounting and alignment system for a medical imaging apparatus, comprising:
   a gantry, including a gantry frame defining an axial centerline, an outer periphery, and a cylindrical-shaped inner circumference defining a patient imaging passage;
   a mounting rail coupled to the gantry between the outer periphery and the inner circumference of the gantry frame, the mounting rail having a rail central axis oriented parallel to the axial centerline of the gantry frame;
   a detector head pivotally coupled to the mounting rail, having a range of pivotal motion about a detector pivot axis that is parallel to the rail central axis, the detector head having a photon detector surface facing the axial centerline of the gantry frame; and
   a locking mount of the detector head, coupling the detector head and the gantry frame, for selectively locking the detector head at any desired fixed position within its range of pivotal motion.

2. The mounting and alignment system of claim 1, further comprising a detector bearing, selectively slidable along axial length of the mounting rail, pivotally coupling the detector head to the mounting rail.

3. The mounting and alignment system of claim 2, further comprising a first axial stop-block coupled to the mounting rail, for limiting axial travel of the detector bearing along the axial length thereof.

4. The mounting and alignment system of claim 2, further comprising:
   the mounting rail defining a cylindrical-profile surface portion; and
   the detector bearing having a sector-shaped cross-sectional profile, an inner circumferential surface of the bearing circumscribing the cylindrical-profile surface portion of the mounting rail, an outer peripheral surface of the bearing coupled to the detector head, and mutually opposed, spaced stop surfaces of the bearing respectively abutting the mounting rail at respective extreme terminus positions along the pivotal range of motion of the detector head.

5. The mounting and alignment system of claim 1, further comprising:
the detector head having opposed first, and second axial ends; and
a radial alignment block, coupled to one of the axial ends of the detector head, having a radial alignment axis normal to the photon detector surface, for selectively aligning the photon detector surface transversely normal to the axial centerline of the gantry frame.

6. The mounting and alignment system of claim 5, further comprising a radial alignment-block recess formed each of the respective first and second axial ends of the detector head, for receiving the radial alignment block therein.

7. The mounting and alignment system of claim 6, further comprising a pair of detector heads commonly pivotally mounted on the mounting rail, the pair of detector heads axially separated by a second axial stop-block interposed therebetween, with the radial alignment block received within and sandwiched between opposed radial alignment-block recesses of abutting axial ends of each detector head, so that selective pivoting positioning and locking of one of the pair of detector heads at any desired fixed position within its range of pivotal motion correspondingly locks the other detector head in the same fixed position.

8. The mounting and alignment system of claim 1, the locking mount further comprising an eccentric coupled to the detector head and the gantry frame, so that pivoting motion of the eccentric correspondingly pivots the detector head about the detector pivot axis through its corresponding pivotal range of motion.

9. The mounting and alignment system of claim 8 further comprising means for locking the eccentric at any desired fixed position within its range of pivotal motion.

10. The mounting and alignment system of claim 1, further comprising:
a plurality of circumferentially spaced mounting rails coupled to the gantry frame, each respective rail axis oriented parallel to and identically radially spaced from the axial centerline of the gantry frame;
a first axial stop-block coupled to each respective mounting rail, commonly aligned along a first axial-stop plane that is normal to the axial centerline of the gantry frame;
a first detector head coupled to each mounting rail, abutting the corresponding first axial stop-block, so that the corresponding detector surface of each of the respective first detector heads is axially aligned along the first axial-stop plane;
a second detector head coupled to each mounting rail, commonly pivotally mounted on the mounting rail along with the respective first detector head, the pair of first and second detector heads on each mounting rail axially separated by a respective second axial stop-block interposed therebetween, so that the corresponding detector surface of each of the respective second detector heads is axially aligned along a second axial-stop plane that is axially spaced from and parallel to the first axial-stop plane;
a plurality of radial alignment blocks respectively coupled to opposing axial ends of its corresponding first and second detector heads, each respective radial alignment block having a radial alignment axis normal to the photon detector surface, for selectively aligning the respective photon detector surfaces of both of the first and second detector heads transversely normal to the axial centerline of the gantry frame; and
each mounting rail location having at least one dedicated locking mount coupled to at least one of the first or the second detector heads, for selectively locking the respective photon detector surfaces of both of the first and second detector heads at any desired fixed position within their respective ranges of pivotal motion.

11. The mounting and alignment system of claim 10, further comprising:
each mounting rail defining a cylindrical-profile surface portion; and
each detector bearing having a sector-shaped cross-sectional profile, an inner circumferential surface of the bearing circumscribing the cylindrical-profile surface portion of the mounting rail, an outer peripheral surface of the bearing coupled to the detector head, and mutually opposed, spaced stop surfaces of the pivot bearing respectively abutting the mounting rail at respective extreme terminus positions along the pivotal range of motion of the detector head.

12. The mounting and alignment system of claim 10, comprising a medical imaging apparatus having at least two axially tandem gantry frames sharing a common coaxial axial-centerline, each of respective pluralities of corresponding tandem-oriented pairs of circumferentially spaced mounting rails of each gantry coaxially registered so that they share a common, coaxial rail axis that is oriented parallel to and identically radially spaced from the common coaxial axial-centerline of the gantry frames, so that detector surfaces of all of the detector heads of each gantry are all equally axially spaced relative to each other in a uniform grid pattern, and that all detector surfaces are transversely normal to the axial centerline of the gantry frame along a common radius and radial length.

13. The mounting and alignment system of claim 12, further comprising:
each mounting rail defining a cylindrical-profile surface portion;
each detector bearing having a sector-shaped cross-sectional profile, an inner circumferential surface of the bearing circumscribing the cylindrical-profile surface portion of the mounting rail, an outer peripheral surface of the bearing coupled to the detector head, and mutually opposed, spaced stop surfaces of the bearing respectively abutting the mounting rail at respective extreme terminus positions along the pivotal range of motion of the detector head.

14. The mounting and alignment system of claim 13, further comprising:
at least one of the locking mounts having an eccentric coupled to a corresponding detector head and the gantry frame, so that pivoting motion of the eccentric correspondingly pivots the corresponding detector head about its pivot axis through its corresponding pivotal range of motion; and
means for locking the eccentric so that the corresponding detector head is selectively locked at any desired fixed position within its range of pivotal motion.

15. The mounting and alignment system of claim 12, further comprising:
each respective first detector head abutting a first side of the corresponding first axial stop-block;
a third detector head coupled to each mounting rail, abutting a second side of the corresponding first axial stop-block, so that the corresponding detector surface of each of the respective third detector heads is axially aligned along a third axial-stop plane that is axially spaced from and parallel to the first and second axial-stop planes;

a fourth detector head coupled to each mounting rail, commonly pivotally mounted on the mounting rail along with the respective third detector head, the pair of third and fourth detector heads on each mounting rail axially separated by a respective third axial stop-block interposed therebetween, so that the corresponding detector surface of each of the respective fourth detector heads is axially aligned along a fourth axial-stop plane that is axially spaced from and parallel to the third axial-stop plane; and a plurality of the radial alignment blocks coupled to respective opposing axial ends of the third and fourth detector heads, each respective radial alignment block having a radial alignment axis normal to the photon detector surface, for selectively aligning the respective photon detector surfaces of both of its corresponding third and fourth detector heads transversely normal to the axial centerline of the gantry frame; and each mounting rail location having another of the at least one dedicated locking mount coupled to at least one of the third or the fourth detector heads, for selectively locking the respective photon detector surfaces of both of the third and fourth detector heads at any desired fixed position within their respective ranges of pivotal motion.

16. A method for mounting and aligning a detector in a gantry of a medical imaging apparatus, comprising:

coupling a mounting rail, having a rail central axis, to a gantry frame, between an outer periphery and a cylindrical-shaped inner circumference of the gantry frame, the gantry frame defining a patient imaging passage, with the mounting rail central axis oriented parallel to an axial centerline defined by the gantry frame;

coupling a first axial stop-block to the mounting rail intermediate first and second ends of the rail;

pivotally coupling a first detector head to a first detector bearing, the first detector head having a range of pivotal motion about a first detector pivot axis, the first detector head having a first photon detector surface, and a first radial alignment block having a first radial alignment axis normal to the first photon detector surface, the first radial alignment block selectively aligning the first photon detector surface transversely normal to the axial centerline of the gantry frame;

inserting the first detector bearing on the first end of the mounting rail, and sliding the bearing along the rail until it abuts the first axial stop-block, the first detector head oriented on the mounting rail with the first detector pivoting axis parallel to the rail central axis and the first photon detector surface facing the axial centerline of the gantry frame;

pivoting the first detector head, while aligning the first photon detector surface with the first radial alignment block, so that the first photon detector surface is oriented transversely normal to the axial centerline of the gantry frame; and locking the first detector head in fixed position, with a locking mount coupled thereto, after the first photon detector surface is oriented transversely normal to the axial centerline of the gantry frame.

17. The method for mounting and aligning a detector of claim 16, further comprising:

coupling a second axial stop-block to the mounting rail, abutting the first detector head;

pivotally coupling a second detector head to a second detector bearing, the second detector head having a range of pivotal motion about a second detector pivot axis, the second detector having a second photon detector surface, and a second detector receiving cavity for receiving therein the first radial alignment block, the second detector receiving cavity having a second radial alignment axis normal to the second photon detector surface; and inserting the second detector bearing on the first end of the mounting rail, and sliding the second detector bearing along the rail until it abuts the second axial stop-block and receives the first radial alignment block within the second detector receiving cavity, so that the second detector head is oriented on the mounting rail with the second detector pivoting axis parallel to the rail central axis and the second photon detector surface facing and oriented transversely normal to the axial centerline of the gantry frame, without need to perform independent pivoting alignment of the second detector head.

18. The method for mounting and aligning a detector of claim 17, further comprising:

commonly fabricating a plurality of stacked gantry backplanes, having commonly co-registered mounting-rail affixation surfaces spaced about a respective circumference thereof;

coupling the commonly fabricated gantry backplanes within the gantry frame, axially spaced along the axial centerline of the gantry frame;

coupling a plurality of the mounting rails, each with a respective first axial stop-block identically axially aligned thereupon, to respective mounting-rail affixation surfaces of the backplanes, circumferentially spaced about the gantry frame, each respective rail axis oriented parallel to and identically radially spaced from the axial centerline of the gantry frame, each respective first axial stop commonly aligned along a first axial stop-plane that is normal to the axial centerline;

inserting and sliding a respective first detector bearing and its coupled first detector head along each respective mounting rail, abutting a first side of its corresponding first axial stop-block, so that the corresponding first detector surface of each of the respective first detector heads is axially aligned along the first axial-stop plane;

aligning each respective first photon detector surface with its corresponding first radial alignment block, so that it is oriented transversely normal to the axial centerline of the gantry frame and locking the first detector head, after the first photon detector surface alignment, in aligned, fixed position with the respective locking mount coupled thereto;

respectively coupling the second axial stop-block to each respective mounting rail, abutting its respective first detector head;

inserting, sliding, and pivoting a respective second detector bearing and its coupled second detector head along each respective mounting rail, abutting its corresponding second axial stop-block, while receiving its respective first radial alignment block within its second detector receiving cavity, so that the corresponding second detector surface of each of the respective second detector heads is axially aligned along a second axial-stop plane, and the second photon detector surface faces and is oriented transversely normal to the axial centerline of the gantry frame, without need to perform independent pivoting alignment of the second detector head.

19. The method for mounting and aligning a detector of claim 18, further comprising:
- pivotally coupling a plurality of third detector heads to respective third detector bearings and a plurality of fourth detector heads to respective fourth detector bearings;
- inserting a respective third detector bearing on the second end of each respective mounting rail, and sliding that bearing on the rail until it abuts the second side of the first axial stop, so that a corresponding third detector surface of each of the respective third detector heads is axially aligned along a third axial-stop plane that is axially spaced from and parallel to the first and second axial-stop planes, the third detector having a third detector-receiving cavity that captures a second radial alignment-block, the second radial alignment-block having a second radial alignment axis normal to the third photon detector surface, for selectively aligning the third photon detector surface transversely normal to the axial centerline of the gantry frame;
- pivoting the third detector head, while aligning the third photon detector surface with the second radial alignment-block, so that it is oriented transversely normal to the axial centerline of the gantry frame; and
- locking the third detector head, after the third photon detector surface alignment, in aligned, fixed position with a second locking mount coupled thereto;
- coupling a third axial stop-block to the mounting rail, abutting the third detector head;
- inserting a respective fourth detector bearing on the second end of each respective mounting rail, and sliding that bearing along the rail until it abuts the third axial stop-block and receives the second radial alignment-block within a fourth detector-receiving cavity thereof, so that a corresponding fourth detector surface of each of the respective fourth detector heads is axially aligned along a fourth axial stop-plane that is axially spaced from and parallel to the first, second and third axial-stop planes, and the fourth photon detector surface facing and oriented transversely normal to the axial centerline of the gantry frame, without need to perform independent pivoting alignment of the fourth detector head.

20. The method for mounting and aligning a detector of claim 19, further comprising coupling two axially tandem gantry frames so that they share a common coaxial axial-centerline, each of respective pluralities of corresponding tandem-oriented pairs of circumferentially spaced mounting rails of each gantry coaxially registered so that they share a common coaxial-rail axis that is oriented parallel to and identically radially spaced from the common coaxial axial-centerline of the gantry frames, so that detector surfaces of all of the detector heads of each gantry are all equally axially spaced relative to each other in a uniform grid pattern of axially aligned columns and circumferentially aligned rows, with all detector surfaces oriented transversely normal to the axial centerline of the gantry frames along a common radius and radial length.

* * * * *